US00PP15189P3

(12) United States Plant Patent
Barendse

(10) Patent No.: US PP15,189 P2
(45) Date of Patent: Sep. 28, 2004

(54) ***GARDENIA* PLANT NAMED 'KIMBERLY'**

(50) Latin Name: *Gardenia jasminoides Ellis*
Varietal Denomination: Kimberly

(76) Inventor: Nicolaas Wilhelmus Jozef Maria Barendse, Mauritslaan 3, 2685 VC, Poeldijk (NL)

( * ) Notice: Subject to any disclaimer, the term of this patent is extended or adjusted under 35 U.S.C. 154(b) by 0 days.

(21) Appl. No.: 10/230,144

(22) Filed: Aug. 29, 2002

(65) Prior Publication Data

US 2004/0045063 P1 Mar. 4, 2004

(51) Int. Cl.[7] ..... A01H 5/00

(52) U.S. Cl. ..... Plt./255
(58) Field of Search ..... Plt./255

(56) References Cited

PUBLICATIONS

UPOV–Rom hit on 'Kimberly', Plant Variety Database, 2003/03.*

* cited by examiner

*Primary Examiner*—Anne Marie Grunberg
(74) *Attorney, Agent, or Firm*—Richard C. Peet

(57) ABSTRACT

A new and distinct *Gardenia* plant named 'Kimberly' characterized by having dark green glossy leaves, somewhat sinuated leaves, large white flowers, fast growth rate, and good branch production.

2 Drawing Sheets

Latin name of the genus and species of the claimed plant: *Gardenia jasminoides* Ellis.
Variety denomination: Kimberly.

BACKGROUND OF THE INVENTION

The present invention relates to a new and distinct cultivar of *Gardenia* plant, botanically known as *Gardenia jasminoides* Ellis, hereinafter referred to by the cultivar name 'Kimberly'.

The new cultivar originated as a mutant in a controlled breeding program in Poeldijk, The Netherlands. The mutant parent is an unnamed plant of *Gardenia jasminoides* Ellis (unpatented). 'Kimberly' was discovered and selected by the inventor, Nicolaas Wilhelmus Jozef Maria Barendse, as a flowering plant within the progeny of the stated cross in a controlled environment in Poeldijk, The Netherlands.

Asexual reproduction of the new cultivar by tissue culture was first performed in Summer 1998 in Alexandria, Egypt, and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be basic characteristics of 'Kimberly' which in combination distinguish this *Gardenia* as a new and distinct cultivar:

1. dark green glossy leaves;
2. somewhat sinuated leaves;
3. large white flowers;
4. fast growth rate; and
5. good branch production.

'Kimberly' has not been observed under all possible environmental conditions. The phenotype of the new cultivar may vary significantly with variations in environment such as temperature, light intensity, and daylength without any change in the genotype of the plant. The following observations, measurements and values describe the new cultivar as grown in Poeldijk, The Netherlands under conditions which closely approximate those generally used in commercial practice.

Of the many commercial cultivars known to the present inventor, the most similar in comparison to 'Kimberly' is cultivar *jasminoides* 'Ellis'. 'Kimberly' has much bigger, darker, glossier and somewhat sinuated leaves. The flowers of 'Kimberly' are bigger but the plant produces less buds. 'Kimberly' is wider than *jasminiodes* Ellis, produces more branches and the growing speed is approximately twice as high.

BRIEF DESCRIPTION OF THE DRAWING

The accompanying photographic drawings illustrate the overall appearance of the new Gardenia showing the colors as true as is reasonably possible with colored reproductions of this type.

FIG. 1 shows a typical 9 month old plant of 'Kimberly'.

FIG. 2 is a closeup of a flower from 'Kimberly'.

DETAILED BOTANICAL DESCRIPTION

The following observations, measurements and values describe the new cultivar as grown in Poeldijk, The Netherlands under conditions which closely approximate those generally used in commercial practice. The cultivar is grown in a normal commercial greenhouse. Minimum temperature in summer and winter is 22 degrees Celsius. The Ph should be kept low. Tip cutting is practiced in order to produce more branches. Growth retardant Alar (Daminozide) is added. Lowest temperature tolerancy is 3 degrees Celsius, highest is 40 degrees Celsius. No photoperiodic treatments are conducted. Color references are made to The Royal Horticultural Society Colour Chart (R.H.S.), edition 2001, except where general colors of ordinary significance are used. Color values were taken under daylight conditions at approximately 1:00 p.m. in Boskoop, The Netherlands. The age of the plant described is 9 months.

Propagation: Tissue culture.

Plant: General Appearance and Form:

*Height.*—Average: 25 cm.

*Spread.*—Average: 55 cm.

*Branching.*—Freely branching, at the branch-tips, where flowers have bloomed, three new branches are developed from axillary nodes.

*Flowering response.*—Terminal flowers appear at branch-tips, after the branches have stopped growing.

*Flowering season.*—Spring and early summer.

*Winter hardiness/weather tolerance.*—Tropical; grown indoors in western Europe; hardy to USDA zone 10.

*Lastingness of the individual bloom.*—Average: 4 days.

*Rooting habit.*—Roots freely branched with many fine roots.

*Time to initiate roots.*—3 weeks in summer, 5 weeks in winter.

*Time to produce a rooted cutting.*—5 weeks in summer, 7 weeks in winter.

*Crop time.*—Spring and early summer.

*Growth and branching habit.*—Broad upright to spreading, freely branching, forming a dense and compact shrub.

*Fragrance.*—Very strong, sweet and pleasant.

Stem description:

*Length.*—Average 15 cm.

*Diameter.*—Average 4 mm.

*Internode length and color.*—Average internode length 4 cm, young stems are green, RHS 141A; older stems are greyed-green, RHS 194A.

Foliage:

*Overall shape of leaf.*—Ovate to elliptic.

*Apex.*—Acute.

*Base.*—Acuminate.

*Length.*—Average 11 cm.

*Width.*—Average 5.8 cm.

*Margin.*—Wavy.

*Texture.*—Smooth, somewhat leathery, very glossy.

*Durability to stresses.*—High.

*Color of upper surface.*—Mature leaf: Green, closest color between RHS 139A and 147A, but much darker. Immature leaf: Closest to yellow-green, RHS 147A, but greener.

*Color of lower surface.*—Mature leaf: Green, RHS 137B to RHS 137C. Immature leaf: Green, RHS 137C.

*Venation color.*—Upper surface: Yellow-green, RHS 144B. Lower surface: Yellow-green, RHS 144C.

*Petiole.*—Length: Average 2 mm. Diameter: Average: 1.5 mm high and 2.5 mm wide. Color: Green, RHS 143C.

Flowers:

*Flower type and habit.*—Double, salverform with a very short tube (the lower ¼ of the petals is fused, the upper ¾ is free). Apart from the 6 sepals, each flower has an average of 24 petaloids; these are irregularly broad elliptic to obovate with an entire, on some petaloids slightly wavy, margin. The average petaloid length is 2.8 cm, average width 2.2 cm. The immature as well as the mature petaloids are white; RHS 155C. They have a smooth, slightly glossy texture.

*Flower size.*—Average diameter 10 cm, average height 4 cm.

*Overall shape.*—Salverform.

*Average number of flowers per lateral branch.*—3.

*Petals.*—Petal Number: 6. Petal Shape: Broad elliptic. Texture: Smooth, dull. Petal size: Average length 6 cm, average width 3.1 cm.

*Petal color.*—Upper surface: White, RHS 155C, tube green, RHS 142C. Lower surface: White, RHS 155C, tube green, RHS 142C to RHS 142D.

*Stem.*—Average length: 15 cm. Average diameter: 4 mm. Color: Young stems are green, RHS 141A, older stems are greyed-green, RHS 194A. Internode length: 4 cm.

*Bud.*—Rate of opening: Individual flowers open at an independent rate from other individual flowers. Color: Green, RHS 143B to RHS 143 C. Shape: Ovate. Length: Average 4 cm (a few days before opening). Diameter: Average 1.5 cm (a few days before opening).

*Peduncles.*—Average length 1.8 cm, average width 4 mm, peduncles are carry the terminally placed flowers in an angle of 5° or straight on top of the branch, the peduncles are strong. Peduncle green; RHS 143C.

Reproductive organs:

*Stamen.*—Average 2 very rudimentary stamen, usually deformed into petaloids.

*Number.*—2.

*Color.*—White, RHS 155C.

*Seeds.*—Flowers are sterile, no seeds (or fruits) are formed.

*Fruit.*—Flowers are sterile, no fruits (or seeds) are formed.

*Anthers.*—Average of 2 very rudimentary stamens, no anthers detected.

*Pollen.*—None observed.

*Stigma.*—Deeply lobed, lobes acute. Color: Yellow, RHS 8B. Ovary: Color: Green; RHS 143B to RHS 143C.

Disease resistance: Not more susceptible to pests and diseases than other *Gardenia* varieties.

I claim:

1. A new and distinct *Gardenia* plant named 'Kimberly', substantially as illustrated and described herein.

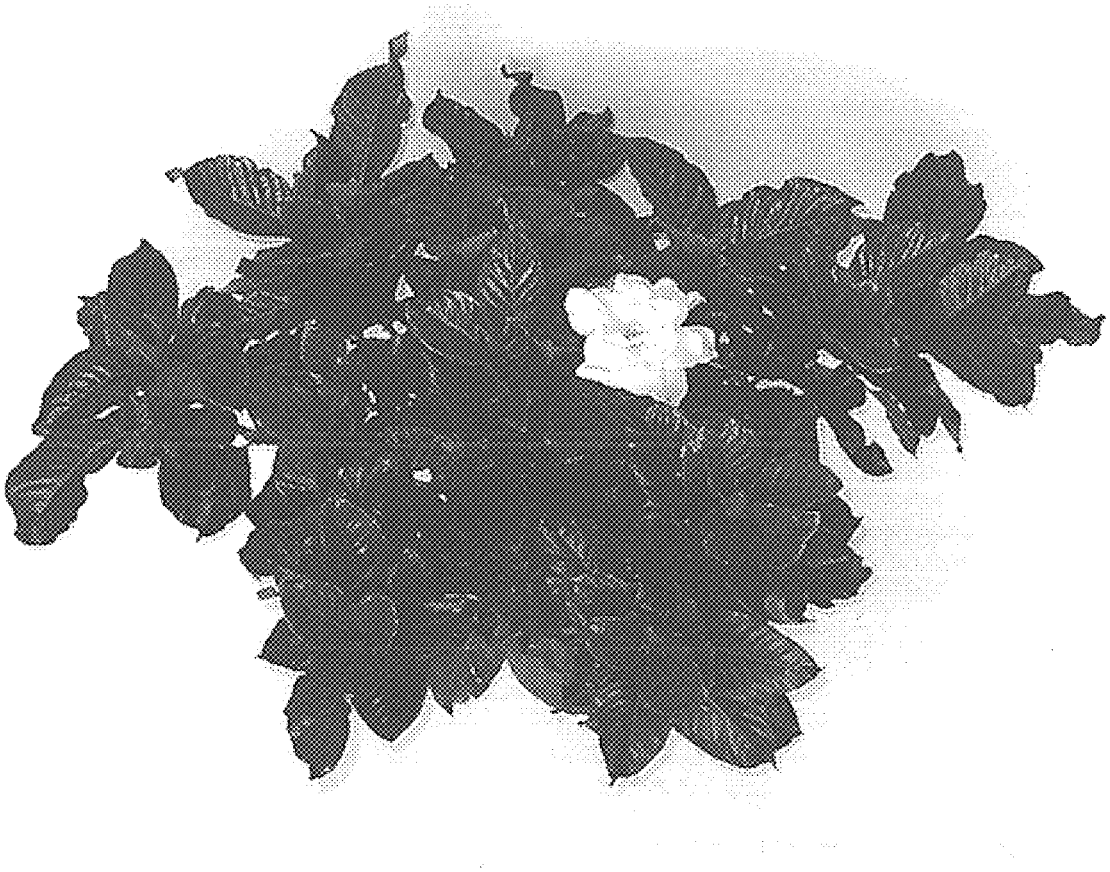

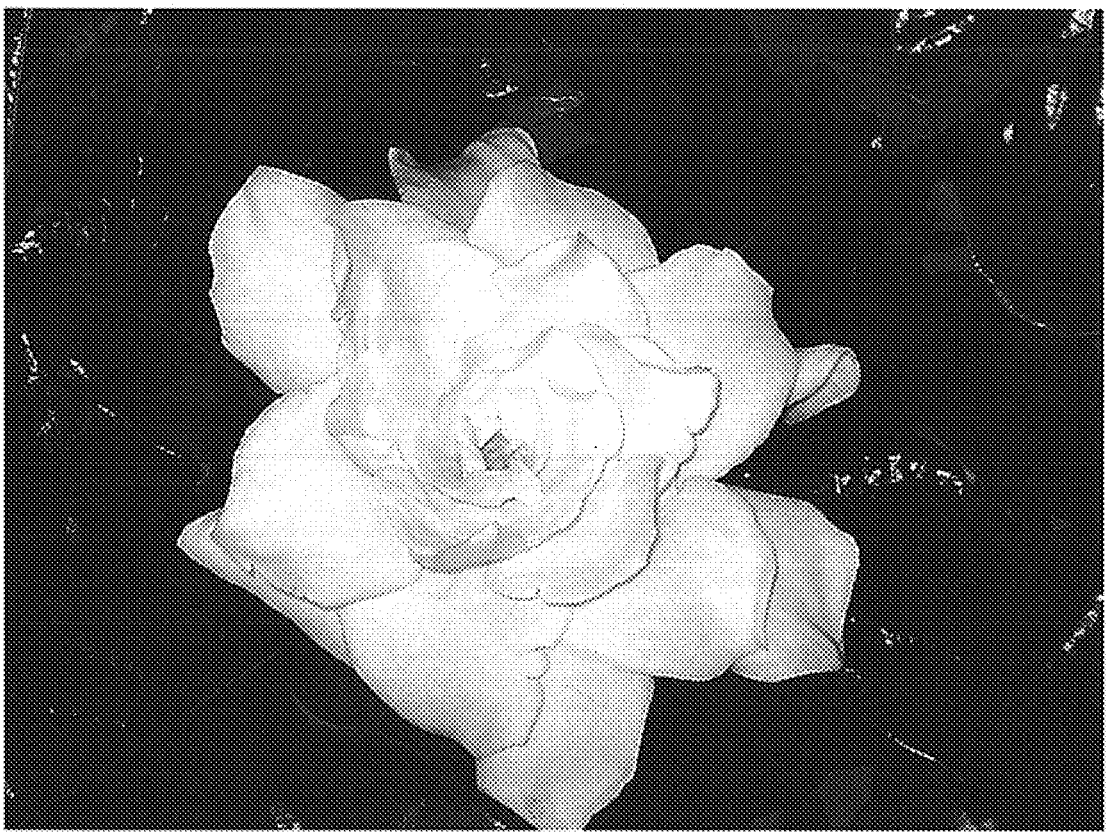

* * * * *